United States Patent [19]

Fein et al.

[11] Patent Number: 5,472,713
[45] Date of Patent: Dec. 5, 1995

[54] THERAPEUTIC USES OF EMU OIL

[75] Inventors: Elaine Fein, Scarsdale, N.Y.; John Caputo, Westport, Conn.; Ann K. Nagal; Karrey-Lynn Nagal, both of Mamaroneck, N.Y.

[73] Assignee: Elf Resources, Inc., New Rochelle, N.Y.

[21] Appl. No.: 344,269

[22] Filed: Nov. 23, 1994

[51] Int. Cl.⁶ ............................................. A61K 35/12
[52] U.S. Cl. .................. 424/522; 424/434; 424/435; 424/436; 424/451; 424/464; 424/489; 514/899
[58] Field of Search ....................... 424/522, 401, 424/434, 435, 436, 451, 464, 489; 514/899

[56] References Cited

FOREIGN PATENT DOCUMENTS 9208470  5/1992  WIPO.

OTHER PUBLICATIONS

"Emu Oil: This Composition Has No Competition"—Emu Today & Tommorrow—Nov. 1994 pp. 16–18 & 20, 22.
"An Analysis Of Emu Oil: Cutting The Fat!"—Emu Today & Tommorrow—Nov. 1994, pp. 131, 133, 135, 138, 139.

*Primary Examiner*—Jyothsna Venkat
*Attorney, Agent, or Firm*—Jordan and Hamburg

[57] ABSTRACT

Emu oil is therapeutically used in methods for lowering cholesterol, triglycerides and low density lipoproteins and increasing high density lipoproteins; preventing and treating allergies; preventing scarring; treating headaches; preventing nose bleeds; treating and preventing cold and flu symptoms; and relieving discomfort associated with menstruation. Additionally, emu oil acts as an effective chemical buffer in combination with glycolic acid.

2 Claims, No Drawings

THERAPEUTIC USES OF EMU OIL

BACKGROUND OF THE INVENTION

The present invention relates to uses of emu oil for preventing and treating a variety of ailments.

Emu oil has been used in Australia as an Aboriginal liniment, the oil being rendered from the bird's fat. The oil is used in cosmetics and cosmetic-related items, including wrinkle-retarding emollients, cosmetic bases and moisturizers for the face and body. It was traditionally used by the Aborigines for treating burns and as a remedy for arthritis and sports injuries. In Australian pharmacies, emu oil is sold as a liniment and a lubricant. Additionally, emu oil is used as a massage oil.

According to one publication, emu oil alone has been unable to reduce inflammation, even though the Aboriginal tribes of Australia have been using emu oil for arthritis. Instead, PCT/AU91/00517, International Publication No. WO 92/08470 found it necessary to add a miscible diluent, such as isopropyl alcohol, amyl alcohol or acetate, ethyl, methyl or isopropylsalicylate, t-tree oil, eucalyptus oil, cineole, or the like, to emu oil to achieve an anti-inflammatory effect.

An important use of emu oil provided by the present invention is for lowering cholesterol for treating high cholesterol conditions. The primary constituents of emu oil are fatty acids. Others have utilized fatty acids for lowering cholesterol and/or for treating high cholesterol conditions.

U.S. Pat. No. 3,849,554 to Winitz uses a defined diet to reduce blood serum cholesterol. The diet includes amino acids, vitamins, minerals, essential fatty acids, including linoleic, linolenic and arachidonic, and carbohydrates, including glucose, maltose, and polysaccharides of glucose. Winitz finds its diet works to reduce blood serum cholesterol principally by controlling the type of carbohydrate in the diet. For example, Winitz finds an increase in cholesterol where sucrose is used.

DiTullio, U.S. Pat. 3,969,508, refers to lowering the concentration of plasma triglycerides using a hypolipidemic composition to produce hypolipidemic activity in hyperlipidemic subjects. The active ingredient used is 4-(2-thenoyl)-2,3-dichlorophenoxy acetic acid. DeTullio finds, as a result of its method, that plasma cholesterol concentrations are not significantly effected and there is no significant effect on free fatty acids.

U.S. Pat. No. 4,472,432 to Iwamura refers to using alpha and beta unsaturated fatty acids from clams to improve lipid metabolism. Specifically, it provides a prophylaxis and remedy of hyperlipidemia and lipotropic effect and prophylaxis of hyterosclerosis arteriosclerosis. Iwamura refers to using 2-octadecenoic acid to decrease total cholesterol, triglyceride and blood serum and total lipid amount in addition to decreasing cholesterol and triglyceride in the liver.

Revici, U.S. Pat. No. 4,513,008 refers to a method of inactivating an enveloped virus, such as herpes, using at least a $C_{20-24}$ linear polyunsaturated acid.

U.S. Pat. No. 4,603,142 to Burger refers to using d-α-tocotrienol in a method for lowering cholesterol. According to Burger, its key ingredient, d-α-tocotrienol, is found in high-protein barley flour and lemon grass oil. Additionally, according to Burger, d-α-tocotrienol inhibits cholesterol biosynthesis.

Ward, U.S. Pat. No. 4,678,808, refers to intravenous emulsions of omega-3 fatty acid esters for supplying essential fatty acids. The omega-3-fatty acid ester of Ward is derived from marine oil. Ward refers to using omega-3-fatty acid esters for treating thrombotic diseases.

U.S. Pat. No. 4,851,437 to Revici refers to using tung oil for treating arteriosclerosis.

Beyer, U.S. Pat. Nos. 4,920,123 and 5,110,817, refer to a method for controlling and/or lowering serum triglyceride and/or serum cholesterol levels in mammals. In its method, Beyer uses pyrazinoylguanidines.

U.S. Pat. No. 4,999,380 to Berger refers to a process of treating lipoprotein disorders associated with cholesterol metabolism using a lipid from the black currant seed to increase high density lipoproteins (HDLs) and decrease low density lipoproteins (LDLs).

Wakabayashi, U.S. Pat. No. 5,034,414, refers to using fish oil fatty acids as an antithrombotic and an antiatherosclerotic.

U.S. Pat. No. 5,277,910 to Hidvégi refers to a process for preparing a pharmaceutical composition for selectively lowering the blood-lipid level. The composition includes saponins from alfalfa.

Mattson, U.S. Pat. No. 4,034,083 and Reissue No. 33,885, refer to compositions for inhibiting the absorption of cholesterol. The composition includes polyesters which act as fat substitutes and are not absorbable or digestible. According to Mattson, the polyesters interfere with the body's absorption of cholesterol. Accordingly, Mattson uses its compositions to treat hypercholesterolemia (high blood cholesterol). Mattson uses fatty acids to make its polyesters.

Jandacek, U.S. Pat. No. 4,005,195 and Reissue No. 33,996, refer to compositions for treating hypercholesterolemia. The compositions referred to in Jandacek include liquid polyol fatty acid polyesters with anti-anal leakage agents. According to Jandacek, the polyesters interfere with the body's absorption of cholesterol. The anti-anal leakage agents are anti-laxative agents, such as a $C_{12}$ or higher saturated fatty acid, for example, cocoa butter, palm oil, etc.

SUMMARY OF THE INVENTION

The present invention is directed to new uses for emu oil. It has been discovered that administration of emu oil on a regular basis results in lowering cholesterol, triglyceride and low density liproproteins (LDL's) and increasing levels of high density lipoproteins (HDL's). Additionally, regular use of emu oil results in improving the rate of growth and condition of nails, preventing and treating allergies, preventing nose bleeds, and preventing and treating headaches (especially migraine headaches). Additionally, emu oil can be used to prevent scarring when applied to a newly received cut or burn. It also diminishes old scars.

Stretch marks, such as those acquired during pregnancy, can be prevented by application of emu oil. Additionally, application of emu oil diminishes or completely erases existing stretch marks.

Emu oil can be administered as necessary for treating cold and flu symptoms, including sore throats and nasal congestion. In the same manner emu oil can be taken as a remedy for the ailments related to menstruation.

Finally, emu oil can be used as a chemical buffer.

It is an object of the present invention to provide methods for the above-described uses of emu oil.

If is a further object of the present invention to provide modes of administration of emu oil for obtaining the benefits described above.

The above and other objects, features and advantages of the present invention will be described herein by a detailed description thereof.

DETAILED DESCRIPTION OF THE INVENTION

Emu oil is obtained from a large, approximately five feet tall, flightless bird of Australia known as an emu, *Dromideius novaehollandiae*. Emus are farmed for their meat, which is low in cholesterol and fat. The oil rendered from the emu is actually a semi-solid fat (i.e., fat and oil mixture) at room temperature, but will herein be referred to as an oil.

The fat and oil mixture is stripped from the carcass of the emu and can be melted to further liquify the oil. Emu oil obtained in this manner is yellow and is olfactorily offensive. It is possible, through refining processes, to remove the yellow color from the oil and reduce its odor. PCT/AU91/00517 refers to removing the yellow color from emu oil by exposing it to sunlight, page 8, and by subjecting it to chemical oxidation by mixing it with benzoyl peroxide in an organic solvent, page 9.

In PCT/AU91/00517 it was found that the remarkable anti-inflammatory effects of the emu oil composition, when mixed with a miscible diluent, disappeared upon removal of the yellow components of the emu oil. Accordingly, PCT/AU91/00517 is directed to using specifically the yellow component of the emu oil along with a miscible diluent. However, the present inventors have found upon refining emu oil to remove the yellow color and reduce its odor, there is no difference in the constituents of the oil, besides its impurities being removed, and the refined oil can be used according to the present invention. Accordingly, for the uses of emu oil in accordance with the present invention either the raw yellow oil or a refined oil can be used.

One type of refined emu oil is manufactured under the trademark KALAYA OIL and can be obtained from New World Technology, Inc. P.O. Box 7580 Greenwich, Conn., 06836-7580. Material Safety Data Sheet Information on such a refined oil are as follows:

| IDENTIFICATION | |
| --- | --- |
| Product Name | EMU OIL |
| UN Number | None Allocated |
| Dangerous Goods Class | None Allocated |
| Subsidiary Risk | None Allocated |
| Hazchem Code | None Allocated |
| Poisons Schedule | Not Scheduled |

TABLE 1

PHYSICAL PROPERTIES

| | | | |
| --- | --- | --- | --- |
| Description: | At 20° C. it is a semi-solid white mass, at 600° C. a practically clear yellow, colored liquid. Very slight odor. | | |
| Boiling Point: | >150° C. | Refractive Index: | 1.4642 |
| Vapor Pressure: | Not available | Acid Value: | 0.45 |
| Specific Gravity: | 0.9458 g/mL | Saponification Value: | 187.09 |
| Flashpoint: | >140° C. | Peroxide Value: | 1.475 |
| Solubility in | insoluble | Iodine Value: | 70.97 |

TABLE 1-continued

PHYSICAL PROPERTIES

| | | | |
| --- | --- | --- | --- |
| Description: | At 20° C. it is a semi-solid white mass, at 600° C. a practically clear yellow, colored liquid. Very slight odor. | | |
| Water: Water Content: | <0.1% w/w | Ester Value: | 186.64 |

TABLE 2

| Constituents (Fatty Acids) | Mean Content (%) |
| --- | --- |
| C14:0 myristic | 0.2 |
| C16:0 palmitic | 30.7 |
| C16:1 palmitoleic | 4.2 |
| C18:0 stearic | 10.7 |
| C18:1 oleic | 46.3 |
| C18:1 elaidic | 0.7 |
| C18:2 linoleic | 6.5 |
| C18:3 (9, 12, 15) linolenic | 0.1 |

| HEALTH HAZARD INFORMATION | |
| --- | --- |
| HEALTH EFFECTS | Emu Oil is an edible oil. |
| INGESTION | Emu Oil is non-irritant. |
| EYES | Emu Oil is non-irritant to mucous membranes. |
| SKIN | Emu Oil at room temperature is non-irritant to most skin types. |
| INHALATION | Emu Oil at room temperature does not present an inhalation hazard. |
| INGESTION | Since Emu Oil is edible, ingestion should not cause problems. |
| INHALATION | Not considered as harmful. |
| PRECAUTIONS FOR USE | |
| EXPOSURE LIMITS | Not considered hazardous. There are no known Threshold Limited Values (TLV) for Emu Oil. |
| VENTILATION | Precautions are not usually required. |
| PERSONAL PROTECTION | Personal protection is not required. |
| FLAMMABILITY | Not considered combustible under 140° C. |
| SAFE HANDLING INFORMATION | |
| STORAGE & TRANSPORT | Emu Oil is an edible oil and should not pose problems with transportation or storage. However, it should not be stored or transported with toxic chemicals, flammable gases, explosives, oxidizing agents and spontaneously combustible substances. Store in a cool area and keep containers closed to avoid contamination from impurities. |
| SPILLS AND DISPOSAL | Contain using sand or earth and use as an absorbent (sand, sawdust, vermiculite) where appropriate. Collect and seal in properly labelled containers for disposal. Wash area down with excess water. Waste material may be incinerated under controlled conditions where permitted. Refer to local Waste Management Authority Regulations for other approved methods. |
| FIRE/EXPLOSION HAZARD | Remove containers from path of fire. Heating can cause expansion and rupture of |

-continued

| | |
|---|---|
| | containers. Keep containers cool with water spray. |
| EXTINGUISHING MEDIA | Carbon dioxide, dry chemical powder, BCF or alcohol stable foam. |

Analysis by Dr. R. B. Longmore, BSc, MSc, PhD (manchr) of the refined oil by gas chromatograph yielded the following information:

TABLE 3

FAME Analysis, relative fatty acid content

| Identity | Name | Mean content (%) | std. dev |
|---|---|---|---|
| C14:0 | myristic | 0.7 | 0.0(3) |
| C16:0 | palmitic | 26.7 | 0.2 |
| C16:1 | palmitoleic | 5.4 | 0.1(3) |
| C18:0 | stearic | 11.3 | 0.3 |
| C18:1 | oleic | 46.1 | 0.8 |
| C18:1 | elaidic | 1.7 one sample detection | |
| C18:2 | linoleic | 8.4 | 0.2 |
| C18:3 | (9,12,15) linolenic | 0.6 | 0.0(1) |

Note:
actual results: sample 1: C18:1 = 46.7%, 0.0% elaidic.
sample 2: C18:1 = 45.6, 1.75% elaidic.
When elaidic not quantified it may be integrated in C18:1 oleic peak.

Further analysis, by ORON Laboratories Pty. Ltd. on Dec. 21, 1993, of physical properties of the refined Emu Oil yielded the following information:

TABLE 4

| TEST | RESULT |
|---|---|
| Weight per mL @ 20° C. | 0.9216 g/mL |
| Refractive Index @ 20° C. | 1.460 |
| Acid Value | 0.40 |
| Saponification Value | 189.84 |
| Iodine Value | 65.83 |
| Peroxide Value | 2.83 |
| Ester Value | 189.44 |
| Water Content | Nil Detected |
| P-Anisidine Value | 2.75 |
| Totox Value | 8.41 |

An independent study on the composition of refined emu oil vs. chicken oil was conducted in August 1993 by Mr. Donald A. Swift. The results of his analysis are reproduced below:

STATEMENT OF ANALYSIS

| | |
|---|---|
| Date of Report | 27 August 1993 |
| Sample | Refined emu oil |
| Description | Colourless semisolid oil; odourless; melts to clear oil |

TABLE 5

FAME Analysis, relative fatty acid content

| Identity | Name | Mean Content (%) | STD Dev |
|---|---|---|---|
| C14:0 | Myristic | 0.0 | 0.0 |
| C16:0 | Palmitic | 22.0 | 0.12 |
| C16:1 | Palmitoleic | 1.3 | 0.12 |
| C18:0 | Stearic | 6.8 | 0.44 |
| C18:1 | Oleic | 62.4 | 1.5 |
| C18:1 | Elaidic | 0.44 | 0.88 |
| C18:2 | Linoleic | 6.9 | 0.41 |
| C18:3 | (9,12,15) Linolenic | 0.0 | 0.0 |

STATEMENT OF ANALYSIS

| | |
|---|---|
| Date of Report | 20 August 1993 |
| Sample | Chicken Oil |
| Description | Straw-coloured semisolid oil; characteristic odour; melts to clear oil |

TABLE 6

FAME Analysis, relative fatty acid content

| Identity | Name | Mean Content (%) | STD Dev |
|---|---|---|---|
| C14:0 | Myristic | 0.8 | 0.0 (1) |
| C16:0 | Palmitic | 14.2 | 1.2 |
| C16:1 | Palmitoleic | 3.3 | 0.38 |
| C18:0 | Stearic | 3.6 | 0.52 |
| C18:1 | Oleic | 66.6 | 1.9 |
| C18:1 | Elaidic | 1.6 | 0.01 |
| C18:2 | Linoleic | 9.3 | 0.28 |
| C18:3 | (9, 12, 15) Linolenic | 0.9 | 0. |

FATTY ACID ANALYSIS OF EMU SUBCUTANEOUS AND INTESTINAL FAT

SAMPLE PREPARATION

Samples of fat from the freezer were cut in sections, and slices cut through the sections to provide representative samples of the fat. The slices were placed in a beaker and microwaved at the lowest setting to melt the fat, with the fat temperature not exceeding 100° C.

One drop of each sample of fat was then placed in a sample tube with 2 drops of T.A.M.H.[1] and 200 µl of toluene. The tube was then shaken, rotated for one hour and then placed in the freezer to await G.C. analysis.

G.C. PARAMETERS

| | |
|---|---|
| Column Type: | HP Ultra |
| Carder Gas: | $H_2$ at 80 KPa |
| Column Length: | 25 meters |
| Column Diameter: | 0.2 mm |
| Initial Temperature: | 195° C. for 18 minutes, then |
| Temperature Rise of 15°^C./minute to the, | |
| Final Temperature of 310° C. for 1 minute | |

TABLE 7

| Fatty Acid | Subcutaneous Fat (#185) | | | Intestinal Fat (#78) | | | Subcutaneous Fat(NT#5) | | |
|---|---|---|---|---|---|---|---|---|---|
| | 1 | 2 | Mean | 3 | 4 | Mean | 5 | 6 | Mean |
| 14:1 | trace | trace | trace | trace | trace | trace | trace | trace | trace |
| 14:0 | 0.5 | 0.5 | 0.5 | 0.4 | 0.5 | 0.4 | 0.3 | 0.3 | 0.3 |
| 16:1 | 2.7 | 2.6 | 2.6 | 3.8 | 3.9 | 3.8 | 4.3 | 4.3 | 4.3 |
| 16:0 | 22.0 | 21.9 | 22.0 | 22.9 | 23.8 | 23.4 | 19.6 | 19.7 | 19.6 |
| 18:2 | 16.3 | 16.4 | 16.4 | 10.0 | 9.9 | 10.0 | 5.8 | 5.8 | 5.8 |
| 18:3 | 0.7 | 0.6 | 0.6 | 0.5 | 0.4 | 0.4 | 0.2 | 0.2 | 0.2 |
| 18:1 (9) | 44.3 | 43.9 | 44.1 | 47.9 | 47.6 | 47.8 | 56.7 | 56.6 | 56.6 |
| 18:1 (7) | 1.8 | 2.0 | 1.9 | 2.9 | 2.5 | 2.7 | 2.5 | 2.4 | 2.4 |
| 18:1 (trans) | 0.3 | 0.4 | 0.4 | 0.4 | 0.3 | 0.4 | 0.2 | 0.1 | 0.2 |
| 18:0 | 10.4 | 10.5 | 10.4 | 10.2 | 10.0 | 10.1 | 10.0 | 10.0 | 10.0 |
| 20:1 | 0.4 | 0.4 | 0.4 | 0.04 | 0.4 | 0.4 | 0.4 | 0.4 | 0.4 |
| Other | 0.6 | 0.8 | 0.7 | 0.6 | 0.7 | 0.6 | 0 | 0.2 | 0.2 |

NOTE:
18:2 and 18:3 percentages were obtained from a small injection of sample (0.2 μL) whilst all other results were from a large injection.
Sample 1, 2, 3, 4 were of white appearance, solid at room temperature whilst samples 5, 6 were of yellow appearance and partially liquid at room temperature.

Additionally, international application PCT/AU91/00517 includes a mass spectral analysis of emu oil and other products in its Table 5. This table is reproduced below as TABLE 8.

TABLE 8

GLC - Mass Spectral Analysis of Emu Oil and Other Products (as % of Total)

| | Identification no. (batch) | | | | | | | | | |
|---|---|---|---|---|---|---|---|---|---|---|
| | 135 | 136 | 137 | 138 | 157 | 158* | 159' | 181 | 203 | 202 |
| Palmitic (C16:0) | 24.1 | 26.0 | 31.1 | 28.2 | 27.3 | 32.0 | 26.5 | 27.5 | 13.2 | 5.6 |
| Palmitoleic (C16:1) | ND | ND | ND | ND | ND | ND | ND | 4.0 | <1.0 | ND |
| Stearic (C18:0) | 10.7 | 11.6 | 9.0 | 10.5 | 9.9 | 11.3 | 9.2 | 8.4 | 2.7 | 1.4 |
| Oleic (C18:1) | 59.9 | 58.1 | 55.2 | 56.6 | 43.7 | 39.8 | 44.2 | 54.2 | 62.4 | 59.9 |
| Linoleic (C18:2) | 5.3 | 4.3 | 4.7 | 4.7 | 7.4 | 6.8 | 8.1 | 5.9 | 20.1 | 23.8 |
| a-Linolenic (C18:3) | ND | ND | ND | ND | 11.7 | 10.1 | 11.9 | ND | 1.7 | 9.1 |
| g-Linolenic (C18:3) | ND | ND | ND | ND | ND | ND | ND | ND | ND | ND |

* -Sediment after cooling EO 157 to 10° C.
' -Supernatant after cooling EO 157 to 10° C.
202 - Canola Brand polyunsaturated cooking oil
ND - Not detectable
" - A commercial preparation of EO diluted with peanut oil (4.1 v/v)

International Application PCT/AU91/00517 also includes a comparison of the fatty acid composition of free range chicken and emu fats in its Table 6. This table is reproduced below as TABLE 9:

TABLE 9

Comparison of Fatty Acid Composition of Free Range Chicken and Emu Fats (Data generated after methoxide hydrolysis and GLC expressed as %).

| Fatty Acid | Number Carbons | Unsaturation | Emu | Chicken |
|---|---|---|---|---|
| Myristic | C14 | 0 | 0.32 | 1.25 |
| Palmitic | C16 | 0 | 21.27 | 22.03 |
| Palmitoleic | C16 | 1 | 5.57 | 6.85 |
| Stearic | C18 | 0 | 7.81 | 5.94 |
| Oleic | C18 | 1 | 54.52 | 48.37 |
| Linoleic | C18 | 2 | 7.24 | 12.06 |
| Linolenic | C18 | 3 | 0.41 | 0.86 |
| Arachidic | C20 | 0 | 0.37 | 0.51 |
| Arachidonic | C20 | 4 | <0.2 | <0.2 |
| Total poly-unsaturated Fatty Acids present | | | 7.65 | 12.92 |

The inventors have found emu oil can be ingested at least once a day for lowering cholesterol and increasing rate of nail growth and condition, e.g., durability of nails. The precise amount of emu oil ingested depends upon several factors including the requirements of the patient and the age and weight of the patient. Though emu oil should be taken daily for obtaining these therapeutic effects, the exact amount of the dosage is not critical, for example, some patients may benefit most from administration of from between two and ten milliliters of the emu oil. Others may find between three and seven milliliters of emu oil beneficial. Still others may ingest between four and six milliliters of emu oil. A preferable dose for adults is one teaspoon of emu oil per day.

Information regarding the use of fatty acids and certain natural oils for lowering cholesterol and treating conditions related to cholesterol metabolism, including, but not limited to, dosages of fatty acids and fat emulsions and forms of administration, are known to those with skill in the art as illustrated by the United States Patents Incorporated herein by reference. The following United States patents are incorporated herein by reference: Winitz U.S. Pat. No. 3,849,554; DiTullio U.S. Pat. No. U.S. Pat. No. 3,969,508; Iwamura U.S. Pat. No. 4,472,432; Revici U.S. Pat No. 4,513,008; Burger U.S. Pat. No. 4,603,142; Ward U.S. Pat. No. 4,678,808; Revici U.S. Pat. No. 4,851,437, Beyer U.S. Pat. Nos. 4,920,123 and 5,110,817; Berger U.S. Pat. No. 4,999,380; Wakabayashi U.S. Pat. No. 5,034,414; Hidvégi U.S. Pat. No.

5,277,910; Mattson U.S. Pat. No. 4,034,083, U.S. Pat. No. Re. 33,885 and Jandacek U.S. Pat. No. 4,005,195, U.S. Pat. No. Re. 33,996, regarding the information referred to in the preceding sentence and the subject matter encompassed by these patents.

Examples 1 and 2 illustrates the cholesterol lowering effects of daily ingestion of emu oil. As can be seen from Examples 1 and 2, emu oil is effective for lowering blood serum cholesterol. The patients in both Examples 1 and 2 have found the effectiveness of emu oil is greatest when it is taken on a regular basis and that the effectiveness of the emu oil for lowering cholesterol diminishes when emu oil is not taken on a regular basis.

EXAMPLE 1

Mature human female aged 38 years ingests approximately 5 drops or one teaspoon of emu oil per day. Prior to this patient's ingestion of emu oil, testing on Jan. 6, 1993 yielded the following results:

| Total cholesterol | 272 mg/dl |
| --- | --- |
| LDL | 193 mg/dl |
| HDL | 58 mg/dl |
| Triglycerides | 103 mg/dl |

Subsequent to ingestion of emu oil, testing yielded the following results: Testing on Feb. 19, 1994, when patient was taking approximately one teaspoon of emu oil per day, but not on a regular basis:

| Total cholesterol | 231 mg/dl |
| --- | --- |
| HDL | 43 mg/dl |
| Chol./HDL | 5 mg/dl |
| LDL | 171 mg/dl |
| Triglycerides | 87 mg/dl |

Testing on May 26, 1994, when patient was taking approximately one teaspoon of emu oil per day on a more regular basis:

| Total cholesterol | 210 mg/dl |
| --- | --- |
| LDL | 132 mg/dl |
| HDL | 66 mg/dl |
| Triglycerides | 58 mg/dl |

EXAMPLE 2

Mature human female aged 60 years ingests 7 to 10 drops of emu oil per day, approximately one teaspoonful. Patient has previously taken Mevocore for lowering her cholesterol and has suffered side effects, including hair loss. Patient does not suffer from side effects from ingesting emu oil and her hair has been restored.

Prior to this patient's ingestion of emu oil, testing on Jul. 27, 1993 yielded the following results:

| Total cholesterol | 292 mg/dl |
| --- | --- |
| HDL | 40 mg/dl |
| Chol./HDL | 7.3 |
| LDL | 205 mg/dl |
| Triglycerides | 233 mg/dl |

Subsequent to ingestion of emu oil of approximately one teaspoon per day, testing on Feb. 2, 1994 yielded the following results:

| Total cholesterol | 264 mg/dl |
| --- | --- |
| HDL | 38 mg/dl |
| Chol./HDL | 7 |
| LDL | 179 mg/dl |
| Triglycerides | 239 mg/dl |

EXAMPLE 3

For the prevention and treatment of allergies, a mature human female aged 60 years, has, for a time period of between six months and one year, coated the inside of her nostrils with the emu oil. As a result, the seasonal allergies she usually suffers have been alleviated.

Examples 4 and 5 illustrate the use of emu oil for preventing scarring.

EXAMPLE 4

A mature human male suffered a deep elongated cut and applied the emu oil to the cut, the expected scar did not result.

EXAMPLE 5

An immature human male aged 13 years impaled his finger on a fish hook. Upon removal of the fish hook emu oil was applied and the expected scar did not result.

Example 6 illustrates the use of emu oil for alleviating headaches. When using emu oil for treating a headache, the emu oil should be applied to the forehead and temples.

EXAMPLE 6

A mature human female having a severe migraine headache applied emu oil to her temples. As a result of applying the emu oil, the patient's migraine was alleviated. Normally, this patient would have to go to her doctor to receive a shot to alleviate her migraine.

Example 7 illustrates the use of emu oil for preventing nose bleeds, especially chronic nosebleeds. Emu oil can be used to prevent nose bleeds by application of a coating of emu oil inside the nostrils.

EXAMPLE 7

Emu oil was applied to the inside of the nostrils of an immature human male who normally has chronic nose bleeds. As a result of using the emu oil, on a daily basis, the usual nose bleeds did not occur.

Examples 8 and 9 illustrate the use of emu oil for preventing and treating cold and flu symptoms.

EXAMPLE 8

A mature human female, aged 60, who normally suffers from bad colds and the flu on a constant basis and who was always on antibiotics, applied emu oil on a regular basis inside her nostrils and ingested approximately one teaspoon per day of emu oil and was able to substantially prevent contraction of a cold or flu. Additionally, when the patient did suffer from congestion, additional application inside her nostrils alleviated her congestion. Further, when the patient did suffer a sore throat, application of emu oil on the back of her tongue alleviated her sore throat.

EXAMPLE 9

On Aug. 23 and 24, 1994 a mature human female, aged 27 years, was able to relieve her sore throat by placing approximately one quarter of a teaspoon of emu oil on her tongue, near the back of her tongue. On Aug. 25, 1994 this patient no longer had a sore throat.

Example 10 illustrates the effectiveness of emu oil for treating premenstrual syndrome (PMS).

EXAMPLE 10

A mature human female aged 38 ingesting emu oil on a regular basis of approximately one teaspoon per day no longer suffers from PMS and is relieved of suffering during her menstrual period. The patient also has a shortened menstrual period. The patient's usual symptoms of PMS and ailments during her menstrual period include stomach cramps, backaches, headaches and painful swelling, all of which the patient no longer suffers.

Emu oil can be used as a chemical buffer. Application of glycolic acid in skin treatments normally causes redness and irritation. The present inventors combined glycolic acid with emu oil, which operated as a buffer, such that the normal redness and irritation experienced upon application of glycolic acid were absent. Example 11 is illustrative of the use of emu oil as a chemical buffer.

EXAMPLE 11

Combined 7% emu oil with 10% glycolic acid in a 2 oz. jar.

Use of the preparation of Example 11 did not cause redness and irritation. Normally, it is not possible to use a preparation containing 10% glycolic acid due to the high level of irritation which results. However, in Example 11, emu oil acts as a chemical buffer to enable use of a preparation containing glycolic acid.

The present invention includes any known means of administration for administering emu oil. Generally known topical, systemic, enteral, rectal, parenteral and oral means of administration for administering emu oil are included in the present invention. Included as modes of administration are ingestion of emu oil by spoon, dropper or gelatin capsule, including time release capsules, directly into the patient's mouth or added to the patient's food. In accordance with the present invention, the patient may ingest an emulsion of emu oil. Accordingly, oral administration of emu oil may be in the form of tablets, capsules, emulsions, suspension, powders, etc., without limitation. Additionally, topical applications of the emu oil are beneficial for preventing and treating scars, preventing and treating headaches (especially migraine headaches), preventing and treating allergies and preventing and treating nose bleeds. Systemic administration may include subcutaneous or intramuscular injections of emu oil alone or in conjunction with a neutral vehicle. For parenteral administration, sterile solutions or emulsions are preferred.

The inventors do not know exactly how emu oil operates to achieve the benefits described above. However, it is hypothesized the effectiveness of emu oil in the Examples outlined above results from it being readily absorbed by the body and operating at a cellular level.

Having described the invention it will be appreciated that the present invention is not limited to that described above and that various changes and modifications can be effected therein by one of ordinary skill in the art without departing from the scope or spirit of the invention as defined by the appended claims.

What is claimed is:

1. A method of decreasing low density lipoproteins comprising administering to a patient an amount of emu oil effective for decreasing low density lipoproteins, wherein the mode of administration is selected from the group consisting of oral, enteral, rectal, parenteral and systemic.

2. The method of claim 1, wherein the effective amount of emu oil is 2–10 milliliters.

\* \* \* \* \*